United States Patent [19]

Oksman et al.

[11] Patent Number: 5,139,325
[45] Date of Patent: Aug. 18, 1992

[54] WIDE DEPTH OF FOCUS POWER ADD TO INTRAOCULAR AND CONTACT LENSES

[76] Inventors: Henry C. Oksman, 20 Wagon Wheel Rd., Mamaroneck, N.Y. 10543; Joseph Eisner, 185 E. 85th St., New York, N.Y. 10028

[21] Appl. No.: 645,896

[22] Filed: Jan. 25, 1991

[51] Int. Cl.$^5$ .............................. G02C 7/04; A61F 2/16
[52] U.S. Cl. .................................... 351/161; 351/177; 623/6
[58] Field of Search ............... 351/160 R, 160 H, 161, 351/162, 177; 623/6

[56] References Cited

U.S. PATENT DOCUMENTS 4,199,231  4/1980  Evans ................................. 351/161

Primary Examiner—Scott J. Sugarman
Attorney, Agent, or Firm—Fiddler Levine & Mandelbaum

[57] ABSTRACT

A lens and method of fabrication thereof for improving reading vision while maintaining normal vision wherein the diopter power of the lens varies inversely with the radius of the lens.

14 Claims, 4 Drawing Sheets

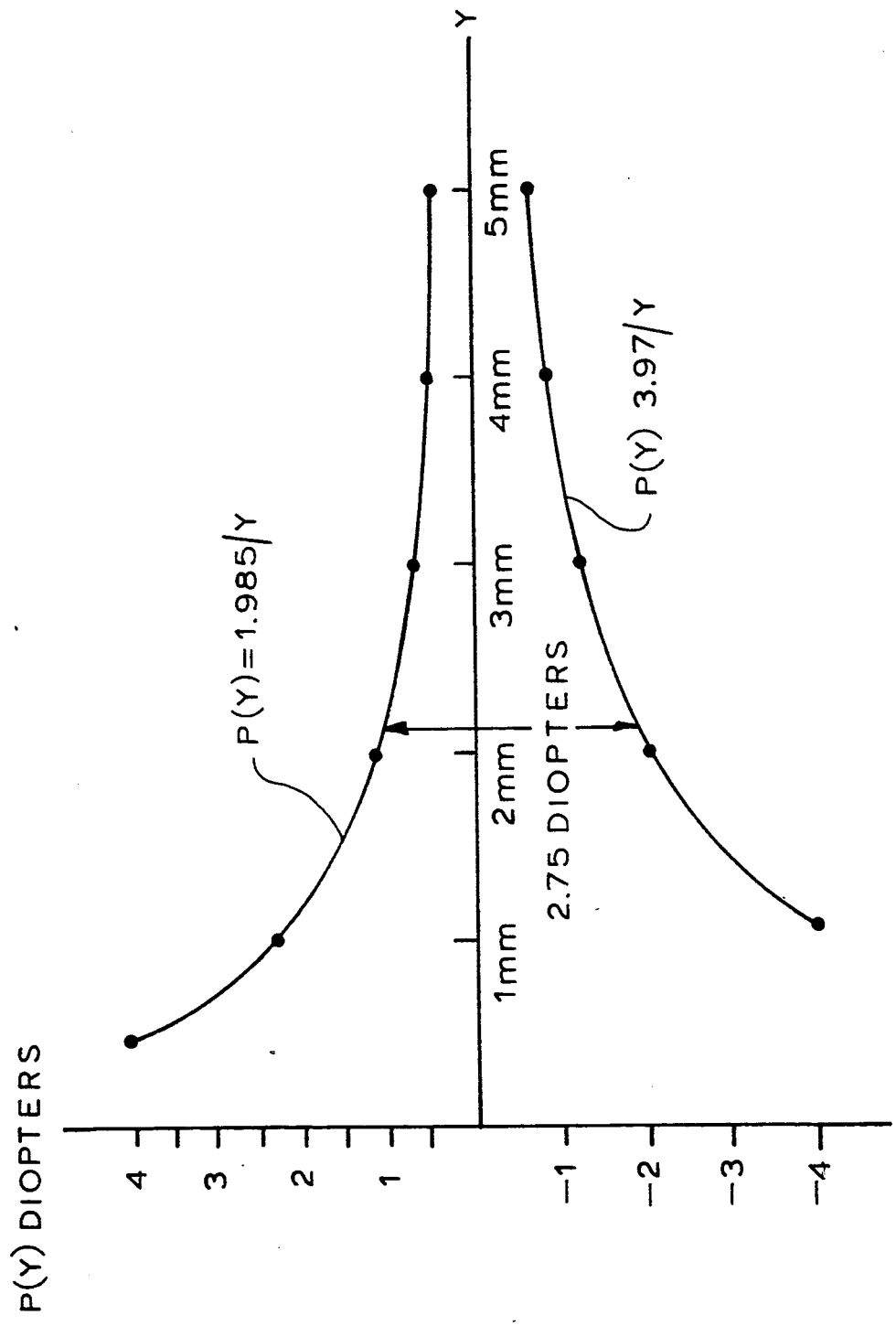

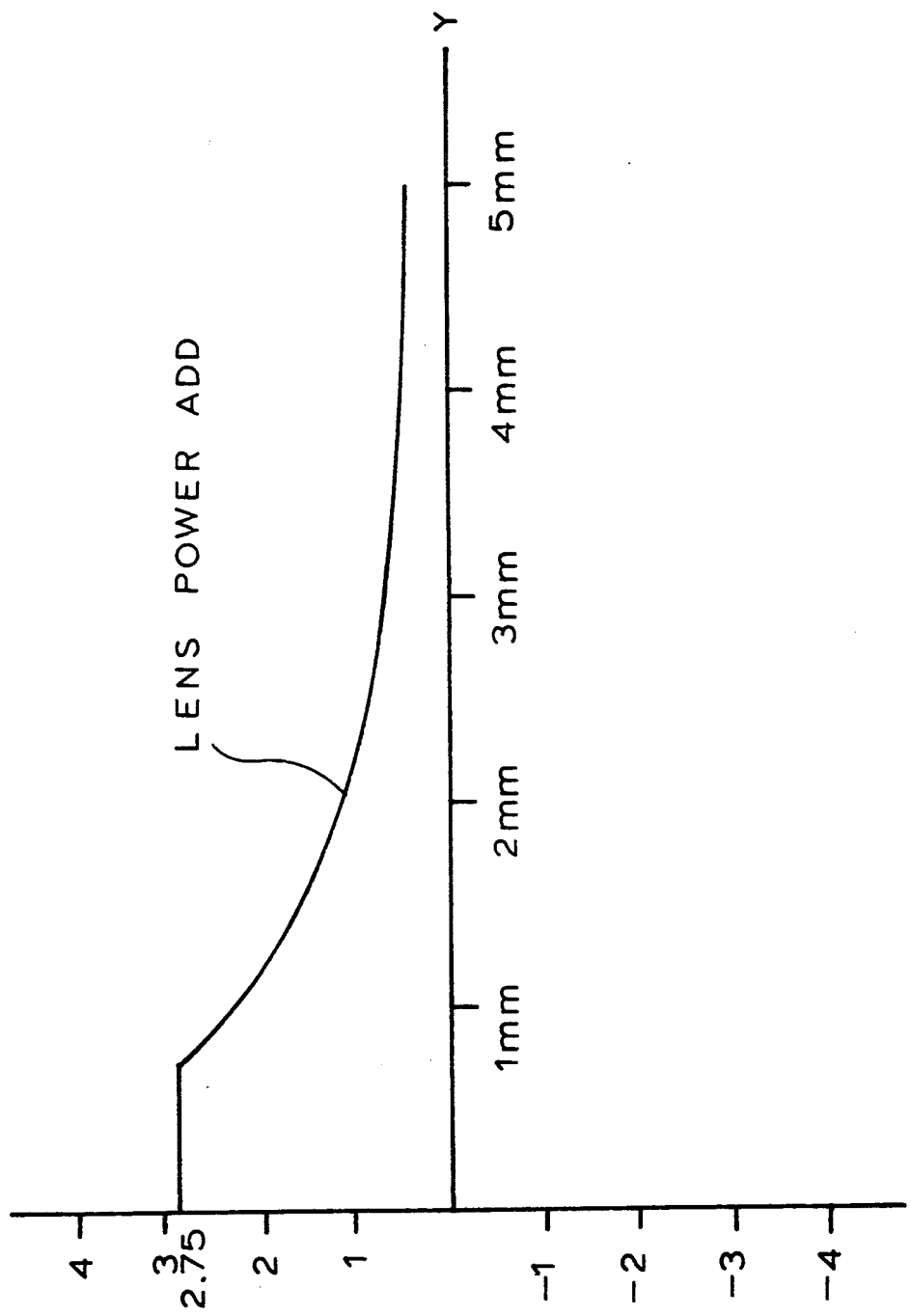

WIDE DEPTH OF FOCUS POWER ADD TO INTRAOCULAR AND CONTACT LENSES

BACKGROUND OF THE INVENTION

It is known in the art of eye care to correct abnormal vision by use of lenses and to alter focus of an image on the retina of the eye. Such lenses can be worn on the surface of the eye as contact lenses or implanted within the eye as intraocular lenses. The lenses can also be used on a camera to enhance depth of focus.

Contact and intraocular lenses attempt to shift the plane of focus to coincide with the retinal plane. In the case of near sightedness, the plane of focus is forward of the retinal plane and the lenses shift the focused image rearwardly toward the retinal plane. In the case of far sightedness, the plane of focus is rearward of the retinal plane and the lenses shift the focused image forwardly toward the retinal plane.

In cases where a patient suffers from both near sightedness when viewing distant objects and far sightedness when viewing near objects, e.g., when reading, lenses which are contoured to remedy one of the deficiencies tend to exacerbate the other. Typically such a patient will be required to use a corrective lens having a negative diopter power in order to obtain desirable distance vision, e.g., 20/20 at infinity. For reading, the patient will be required to add a positive diopter power. However, the addition of the positive diopter power will degrade the distance vision, thereby requiring that the add power lens be removable, e.g., in the form of eye glasses.

SUMMARY OF THE INVENTION

The instant invention overcomes the aforementioned problems of prior art lenses, by enabling a correction to be applied to the normal distance viewing lens power, which enhances near vision while maintaining the normal distance vision, wherein the lens has a vision correction power characteristic which varies inversely as a function of radial distance from the center thereof over at least a portion of the radius and has a power profile according to the function $K \tan \theta / Y$ where $K$ is a constant, $\theta$ is equal to one half the angle subtended by the smallest object to be seen at the viewing distance, and $Y$ is the radial distance from the center of the lens.

It is an therefore object of the invention to provide a lens which can aid both distant and reading vision.

Another object of the invention is to provide a lens which can aid both distant and reading vision by enabling focusing of an image of distant and near objects close to the retinal plane.

Still another object of the invention is to provide a lens for enabling viewing over an extended depth of field.

A further object of the invention is to provide a lens with a power that varies as a function of pupillary aperture.

Other and further objects of the invention will be apparent from the following drawings and description of a preferred embodiment of the invention.

DESCRIPTION OF THE DRAWINGS

FIG. 3 is a graph showing the relationship of distance correction parameters.

FIG. 4 is a graphical view of the power add profile of the lens of the preferred embodiment of the invention.

DESCRIPTION OF THE PREFERRED EMBODIMENT

Monofocal lenses have a depth of focus dependent on the pupillary size and the visual angle tested, i.e., the angle subtended by the object to be viewed at the viewing distance. For example, in order to obtain 20/20 vision, which is equivalent to viewing the letter E through an angle of view of of five minutes of arc, each arm of the E being equivalent to one minute of arc, a pupil one millimeter in diameter has an average depth of focus of 6.6 diopters. For the same 20/20 vision, a pupil 2 millimeters in diameter has an average depth of focus of 4.05 diopters. As pupil size increases beyond 2 millimeters, the diopter value for 20/20 vision decreases rapidly.

We have developed a lens having a variable power profile based on a mathematical function that has been optimized to yield enhanced near vision while maintaining normal distance vision. Distance vision may be maintained irrespective of pupillary size. Corrected reading vision is simultaneously obtained at up to moderate pupillary sizes.

In the preferred embodiment of the invention, the lens has been optimized so that 20/20 distance vision is obtained irrespective of pupillary size and 20/40 reading vision is obtained at pupillary sizes 4.32 mm in diameter or smaller. Compensation for pupillary sizes greater than 4.32 mm in diameter can be made through the use of eye glasses.

The lens design of the preferred embodiment will allow 20/40 as close as 14.3 inches (2.75 diopters). For a pupillary opening of 6 mm, 20/40 vision exists as close as 19.7 inches (2.0 diopters) from the patient's eyes.

Figure 1:
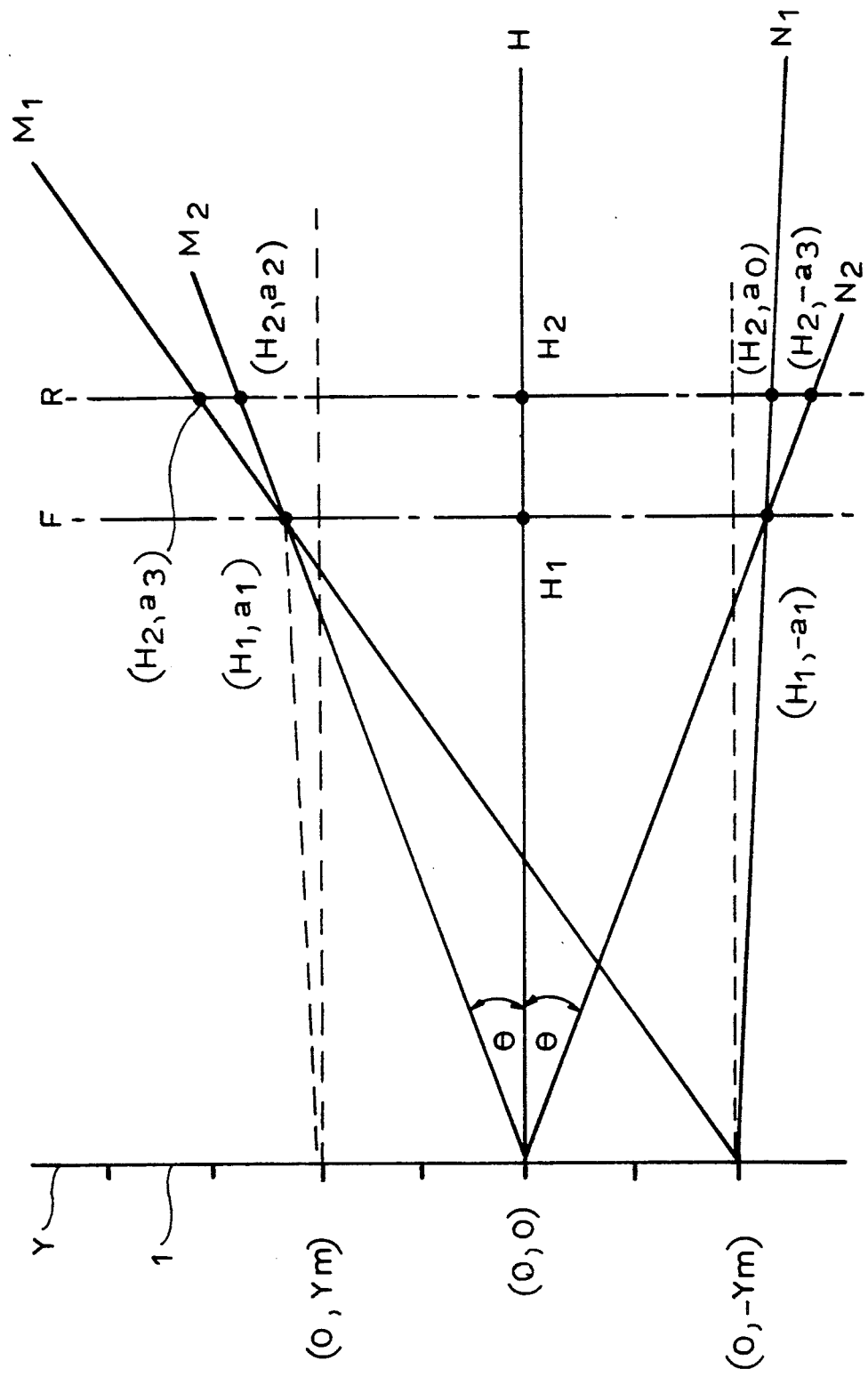
FIG. 1 is a graphical view of the invention of the preferred embodiment in a distance vision environment.

Referring now to FIG. 1 of the drawings there is shown a vertical axis Y representing the radial distance from the center 0 of a lens 1. That is, the origin of the graph is at the center 0 of the lens 1. A horizontal axis H extending from the origin 0 represents distance from the lens 1. The focal plane F intersects the H axis at point ($H_1$,0). The retinal plane R intersects the H axis, behind the focal plane (near sightedness) at point ($H_2$,O).

The lens 1 has a maximum effective radius equal to $Y_m$. Two rays $M_1$ and $M_2$ reflected from the point of lowest extremity on a distant circular object (not shown) having its center on the optical axis H of the lens 1 are focused by the lens 1. Ray $M_1$ passes through the lens 1 at point (O,-$Y_m$), below and at the maximum distance from the center 0 of the lens 1. Ray $M_1$ is focused on the focal plane F at point ($H_1$,$a_1$), in front of the retinal plane R (near sightedness), and on the retinal plane R at point ($H_2$,$a_3$), where $H_2 \geq H_1$. Ray $M_2$ passes through the ter 0 of the lens 1. Ray $M_2$ is also focused on the focal plane F at point ($H_1$,$a_1$), in front of the retinal plane R, but on the retinal plane R at point ($H_2$,$a_2$).

Two rays $N_1$ and $N_2$ reflected from the point of highest extremity on the object are also focused by the lens 1. Ray $N_1$ passes through the lens 1 at point (O,-$Y_m$), the same point as ray $M_1$. Ray $N_1$ is focused on the focal plane at point ($H_1$,-$a_1$), and on the retinal plane R at point ($H_2$,$a_o$). Ray $N_z$ passes through the center 0 of the lens 1. Ray $N_2$ is also focused on the focal plane F at point ($H_1$,-$a_1$), but on the retinal plane R at point ($H_2$,-$a_3$).

Because of similar triangles, $$\frac{a_1}{H_1} = \frac{a_2}{H_2}, \quad (1)$$

and $$\frac{(a_0 - Y_m)}{H_2} = \frac{(a_1 - Y_m)}{H_1}. \quad (2)$$

If the angle between the optical axis H of lens 1 and ray $M_2$, i.e., one half the viewing angle, is defined as $\theta$, then $$\frac{a_2}{H_2} = \frac{a_1}{H_1} = \tan\theta. \quad (3)$$

Combining the above relationships, $$\frac{a_0}{a_2} = 1 - \frac{Y_m}{\tan\theta}\left(\frac{1}{H_1} - \frac{1}{H_2}\right) \quad (4)$$

If v = object to lens distance
u = image to lens distance
n = index of refraction, and
P = lens diopter power, i.e., reciprocal of focal length expressed in meters, then $$v = H_1, \quad (5)$$

and $$\frac{1}{u} + P = \frac{n}{v} \quad (6)$$

assuming free space between lens and object.
By algebraic substitution, it is shown that $$\frac{a_0}{a_2} = 1 - \frac{Y_m}{\tan\theta}\left(\frac{1}{un} + \frac{P}{n} \frac{1}{H_2}\right), a_0 < a_2 \quad (7)$$

and $$\frac{a_3}{a_2} = 1 + \frac{Y_m}{\tan\theta}\left(\frac{1}{un} + \frac{P}{n} - \frac{1}{H_2}\right), a_3 > a_2 \quad (8)$$

Figure 2:
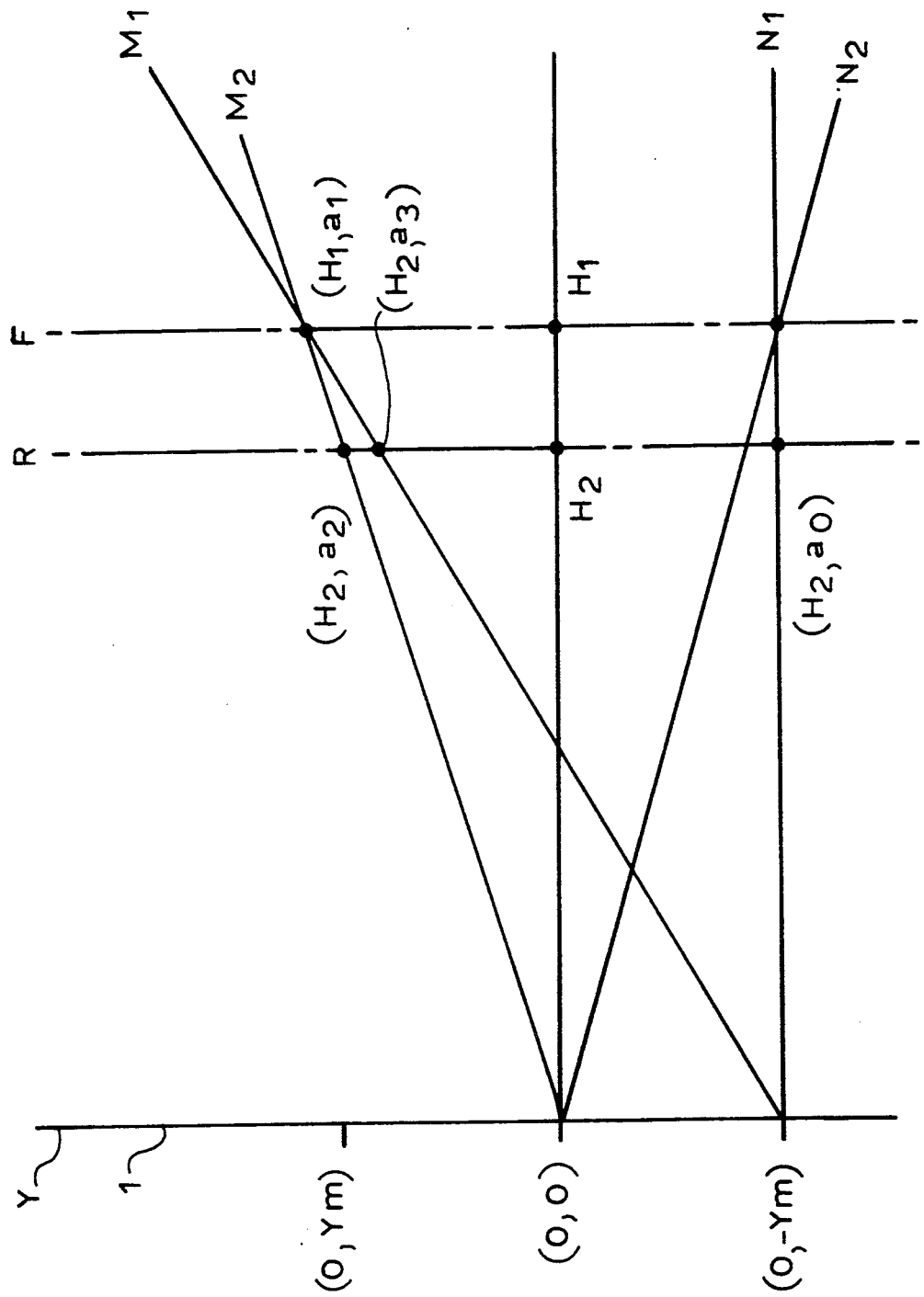
FIG. 2 is a graphical view of the invention of the preferred embodiment in a near vision environment.

Referring now to FIG. 2, a similar situation to that of FIG. 1 is presented except that a near object is being viewed and the focal plane F is behind the retinal plane R (far sightedness). That is, $H_2 \leq H_1$.

Again, Because of similar triangles, $$\frac{a_1}{H_1} = \frac{a_2}{H_2}, \quad (9)$$

$$\frac{(a_3 + Y_m)}{H_2} = \frac{(a_1 + Y_m)}{H_1}, \quad (10)$$

and $$\frac{(a_0 - Y_m)}{H_2} = \frac{(a_1 - Y_m)}{H_1}. \quad (11)$$

Solving algebraically, it is found that equations (7) and (8) still apply.

If R is the radius of the image of the object projected onto the retinal plane, $a_0 + a_3 = 2R$. Also, $R = a_2$.

Let $C = a_3 - R = a_3 - a_2$.

For $H_2 \geq H_1$, C has a positive value and is the maximum displacement between the center of the projected image of the object on the retinal plane and the optical axis of the lens.

$$C = \frac{Ya_2}{\tan\theta}\left(\frac{1}{nu_1} + \frac{P}{n} - \frac{1}{H_2}\right) \quad (12)$$

For $H_2 \leq H_1$, C has a positive value and is the maximum displacement between the center of the projected image of the object on the retinal plane and the optical axis of the lens when $C = a_0 - a_2$.

$$C = \frac{-Ya_2}{\tan\theta}\left(\frac{1}{nu_2} + \frac{P}{n} - \frac{1}{H_2}\right). \quad (13)$$

The depth of focus (DOF) is equal to $$\frac{1}{nu_1} - \frac{1}{nu_2}.$$

Therefore, $$DOF = \frac{2C\tan\theta}{Ya_2} = \frac{2(C/a_2)\tan\theta}{Y},$$

$C/a_2$ being a constant of proportionality = K.
Hence, $$DOF = \frac{K\tan\theta}{Y}$$

where Y is the radial distance of a point in the pupil from the center of the optical axis. Thus it is seen that DOF is inversely proportional to Y.

K may be computed theoretically. However, due to errors contributed by external variables, it has been found more convenient to determine K empirically. We have found that K has a value of approximately 27,300 for 20/20 vision and 13,700 for 20/40 vision. The lens of the preferred embodiment of the invention has been designed to yield distance vision of no worse than 20/20 and near or reading vision of no worse than 20/40.

Referring now to FIG. 3, there is shown a plot of depth of focus (DOF) as a function of pupillary radius for both near and distant vision. The curve above the horizontal axis represents the distance that the focal plane may be in front of the retinal plane for distance vision of 20/20. Depth of focus DOF) varies with pupillary radius (Y) for 20/20 vision in accordance with $$DOF \text{ (diopters)} = 3.97/Y$$

Since one half of the depth of focus is in front of the image plane and the other half behind it, for 20/20 vision, the function plotted for lens diopter power P(Y) above the horizontal axis in FIG. 3 is $$P(Y) \text{ (diopters)} = 1.985/Y.$$

For 20/40 near or reading vision, the function plotted below the horizontal axis in FIG. 3 is P(Y) (diopters) = 3.97/Y.

By adding to the power of a lens designed to give normal, i e. 20/20, distance vision a positive power following the foregoing profile of diopter power as a function of radius, at least 20/20 distance vision will obtain, no matter the pupil size, while reading depth of focus will vary with pupillary size. The lens of the preferred embodiment of the invention will give at least 20/40 reading vision for pupillary diameters up to 4.32 mm at distances as close as 14.3 inches (+2.75 diopters). For a 6 mm pupillary diameter, 20/40 vision will obtain only down to 19.7 inches from the patient's eyes.

From FIG. 3, it is seen that at pupillary radii less than or equal to 0.72mm, a lens having a power of 2.75 diopters when added to the normal optical distance power will suffice to maintain 20/20 distance vision. Hence the function P(Y) = 1.985/Y can be truncated to a constant P(Y) = 2.75 diopters.

At pupillary radii more than .72mm, the power added to the optical distance power to maintain 20/20 vision will be in accordance with the function P(Y) = 1.985/Y.

The add power of the lens of the preferred embodiment of the invention, that is, the power which is added to the power that gives normal 20/20 distance vision, is shown in FIG. 4. P(Y) = 2.75 diopters up to .72 mm and P(Y) = 1.985/Y for pupillary radii of from 0.72mm up to the periphery of the lens.

If the degree of correction is sought to be limited to 3.0 diopters instead of 2.75 diopters, the truncated value of 3.0 diopters can be used at pupillary radii of up to 0.66 mm with the P(Y) = 1.985/Y relationship obtaining at pupillary radii greater than 0.66 mm.

Compensation for anticipated clinical errors may be made merely by subtracting the expected error from the add power, P(Y) thereby lowering the curve above the horizontal axis in FIG. 3. For example, if the anticipated clinical error were 0.3 diopters, the function would be:

Lens power P(Y) = Distance Power + (1.985/Y) − 0.3 diopters.

Under this condition, the 2.75 diopter truncated power would obtain at pupillary radii up to 0.65 mm and thereafter the correction added to the distance power would be (1.985/Y) − 0.3. From FIG. 3, it is seen that this lens would give 20/40 vision for a pupil of up to 3.9 mm diameter. The add power will not reach zero unless the function is truncated.

It is to be appreciated that the foregoing is a description of a preferred embodiment of the invention to which variations and modifications may be made without departing from the spirit and scope of the invention. For example instead of constructing the lens to have a continuous add function, the power add can be done in small discrete regions each of which has a constant power but which have stepped values that approximate the disclosed function.

What is claimed is:

1. A lens for enhancing near vision while maintaining normal distance vision having a power designed to give normal distance vision to which there is added a vision correction power which varies inversely as a function of radial distance from the center thereof wherein the added vision correction power is inversely proportional to said radial distance over at least a portion of said radius where it is equal to K tan θ/Y where K is a constant, θ is equal to one half the angle subtended by the smallest object to be seen at the viewing distance, and Y is the radial distance from the center of the lens.

2. A lens according to claim 1 wherein the vision correction power is constant from the center to said radius portion.

3. A lens according to claim 1 wherein θ is equal to one half minute of arc.

4. A lens according to claim 1 wherein K = approximately 27,300.

5. A lens according to claim 1 wherein K = approximately 13,700.

6. A lens according to claim 2 wherein the correction power is equal to +2.75 diopters at radii up to approximately 0.72 mm.

7. A lens according to claim 1 wherein the correction power is equal to 1.985/Y diopters at radii greater than approximately 0.72 mm.

8. A method of making a lens for enhancing near vision while maintaining normal distance vision comprising adding to the lens distance power a vision correction power inversely proportional to the distance from the center of the lens over at least a portion of a radius of said lens where it is equal to K tan θ/Y where K is a constant, θ is equal to one half the angle subtended by the smallest object to be seen at the viewing distance, and Y is said radial distance.

9. A method according to claim 8 wherein the vision correction power is constant from the center to said radius portion.

10. A method according to claim 8 wherein θ is equal to one half minute of arc.

11. A method according to claim 8 wherein K = approximately 27,300.

12. A method according to claim 8 wherein K = approximately 13,700.

13. A method according to claim 9 wherein the correction power is equal to +2.75 diopters at radii up to approximately 0.72 mm.

14. A method according to claim 9 wherein the correction power is equal to 1.985/Y diopters at radii greater than approximately 0.72 mm.

* * * * *

UNITED STATES PATENT AND TRADEMARK OFFICE
CERTIFICATE OF CORRECTION

PATENT NO. : 5,139,325
DATED : August 18, 1992
INVENTOR(S) : Oksman, et al.

It is certified that error appears in the above–identified patent and that said Letters Patent is hereby corrected as shown below:

At column 2, line 59, change "ter" to -- center --.

At column 2, line 67, change "$N_z$" to -- $N_2$ --.

At column 4, line 57, before "DOF", insert -- ( --.

Signed and Sealed this

Seventeenth Day of August, 1993

Attest:

BRUCE LEHMAN

Attesting Officer

Commissioner of Patents and Trademarks